United States Patent
Han et al.

(10) Patent No.: US 11,541,184 B2
(45) Date of Patent: Jan. 3, 2023

(54) FAT SUCTION AND GRAFT SYRINGE HAVING NEGATIVE PRESSURE ADJUSTMENT MEANS

(71) Applicant: NANUMCOMPANY CO., LTD., Daegu (KR)

(72) Inventors: Kum Bok Han, Sokcho-si (KR); Yong Hwan Choi, Seoul (KR)

(73) Assignee: NANUMCOMPANY CO., LTD., Daegu (KR)

( * ) Notice: Subject to any disclaimer, the term of this patent is extended or adjusted under 35 U.S.C. 154(b) by 198 days.

(21) Appl. No.: 17/042,144

(22) PCT Filed: Jul. 26, 2019

(86) PCT No.: PCT/KR2019/009306
§ 371 (c)(1),
(2) Date: Sep. 27, 2020

(87) PCT Pub. No.: WO2020/027504
PCT Pub. Date: Feb. 6, 2020

(65) Prior Publication Data
US 2021/0008290 A1 Jan. 14, 2021

(30) Foreign Application Priority Data
Jul. 31, 2018 (KR) .......... 10-2018-0088914

(51) Int. Cl.
*A61M 5/315* (2006.01)
*A61M 1/00* (2006.01)
*A61M 5/31* (2006.01)

(52) U.S. Cl.
CPC .......... *A61M 5/31515* (2013.01); *A61M 1/67* (2021.05); *A61M 1/81* (2021.05);
(Continued)

(58) Field of Classification Search
CPC ............ A61M 5/3148; A61M 5/31501; A61M 5/31505; A61M 2005/31506; A61M 2005/31508; A61M 2005/3151
See application file for complete search history.

(56) References Cited

U.S. PATENT DOCUMENTS

| 5,380,295 A | 1/1995 | Vacca |
| 2015/0045740 A1* | 2/2015 | Kojima ............. A61M 5/31505 604/220 |
| 2015/0105754 A1* | 4/2015 | Roche ..................... A61M 1/67 604/542 |

FOREIGN PATENT DOCUMENTS

| CN | 105263548 A | 1/2016 |
| FR | 2536285 A1 * | 11/1982 |

(Continued)

OTHER PUBLICATIONS

English Translation of the Description of JP-05317423-A. Accessed from Espaceneton Jun. 17, 2022 (Year: 1993).*

*Primary Examiner* — Amber R Stiles
*Assistant Examiner* — Leah J Swanson
(74) *Attorney, Agent, or Firm* — Rabin & Berdo, P.C.

(57) ABSTRACT

A fat suction and graft syringe includes a negative pressure adjustment mechanism. The negative pressure state in a barrel can be maintained during a procedure only by pulling and releasing a plunger, and only by slightly rotating the plunger. The plunger can be pushed inside the barrel without being constrained by a multi-level holding plate and a single-surface rotation clip, whereby the syringe has enhanced convenience in the use and production thereof so that many practitioners accustomed to using a normal syringe can easily use the syringe without separately learning how to manipulate the syringe.

7 Claims, 10 Drawing Sheets

(52) U.S. Cl.
CPC ...... *A61M 5/3148* (2013.01); *A61M 5/31501* (2013.01); *A61M 5/31581* (2013.01); *A61M 2202/08* (2013.01)

(56) References Cited

FOREIGN PATENT DOCUMENTS

| | | | | | |
|---|---|---|---|---|---|
| GB | 2187388 | A | * | 9/1987 | .......... A61M 5/3156 |
| JP | 05317423 | A | * | 12/1993 | ........ A61M 5/31501 |
| JP | 5819295 | B2 | | 11/2015 | |
| KR | 101113752 | B1 | * | 4/2012 | |
| KR | 101113752 | B1 | | 4/2012 | |
| KR | 101707475 | B1 | | 2/2017 | |
| KR | 101742905 | B1 | | 5/2017 | |
| WO | 2013161435 | A1 | | 10/2013 | |
| WO | WO-2018100445 | A1 | * | 6/2018 | |

\* cited by examiner

FAT SUCTION AND GRAFT SYRINGE HAVING NEGATIVE PRESSURE ADJUSTMENT MEANS

TECHNICAL FIELD

The present invention generally relates to a fat suction and graft syringe. More particularly, the present invention relates to a fat suction and graft syringe having a negative pressure adjustment means, wherein the negative pressure adjustment means is provided with a multi-level holding plate composed of at least one plate vertically arranged in inner space between partition walls of a plunger and dividing the inner space between the partition walls into multi-level areas; a single-surface rotation clip configured to be coupled to a side of the entrance of a barrel and having a bent part which is rotated only upward and is not rotated downward; and a holding plate avoidance part supplying space allowing pressure applied to the single-surface rotation clip by the multi-level holding plate to be removed such that the single-surface rotation clip is moved to the space, whereby during fat suction and grafting procedures, the state of negative pressure inside the barrel is maintained only by pulling and releasing the plunger, and the multi-level holding plates do not interfere with the single-surface rotation clip only by slightly rotating the plunger such that the plunger is pushed inside, thereby improving usability such that many medical practitioners accustomed to the use of a normal syringe can easily use the syringe having the negative pressure adjustment means even without separately learning how to manipulate the syringe, and improving manufacturability.

BACKGROUND ART

Recently, as interest in beauty and desire for anti-aging has increased, demand for various cosmetic procedures such as fat suction and grafting is increasing.

In the case of such cosmetic procedures, the individual competence of a medical practitioner performing the procedure was relied upon in the past, but in recent years, demand has been increasing for various instruments that can improve the convenience and efficiency of the procedure such that a medical practitioner performing the procedure can promote the safety of a person being treated.

In particular, in the case of a syringe used for fat suction, unlike a syringe used only for injecting drugs, a plunger of a syringe is moved rearward to create space in which fat can be filled inside a barrel, and while a medical practitioner manipulates the syringe to suction fat from a person's body, the state of negative pressure inside the syringe allowing the fat to be suctioned into the syringe is required to be maintained.

In this case, the forcible suction of the fat may be performed by a separate suction means, but in that case, surrounding tissues may be damaged due to excessive suction power. Accordingly, it is preferable to naturally suction fat due to pressure difference while the state of negative pressure is maintained inside a fat suction and graft syringe.

To this end, during fat suction, the state of negative pressure is required to be maintained while the plunger is prevented from being pulled inside due to the pressure difference, so while the plunger pulled rearward is held with palms and fingers, a needle is positioned.

However, for small syringes of 10 cc or 30 cc, the negative pressure of an inner space defined between the end of a plunger and the end of a barrel is not large, so during fat suction, a medical practitioner may hold the plunger without difficulty. However, for large syringes of 50 cc or 100 cc, negative pressure produced in an inner space between the end of a plunger and the end of a barrel is increased significantly, so it is not easy to manipulate a syringe while the barrel is held with one hand and the plunger is held with the other hand during fat suction.

Accordingly, to solve the inconvenience that a medical practitioner is required to use his or her physical power to maintain the state of negative pressure of the syringe during fat suction, there have been various attempts maintaining the state of negative pressure in inner space between the end of the plunger and the end of the barrel by maintaining the state of the plunger pulled rearward such that fat is easily suctioned into the space.

As a part of these attempts, there is proposed a disposable syringe for fine needle aspiration cytology in Korean Patent No. 10-1742905. The disposable syringe for fine needle aspiration cytology includes a position holding means provided with a plurality of holding protrusions holding a relative position of the plunger to the barrel, and a stopper determining a position. However, the position holding means having considerable volume, which is proposed in Korean Patent No. 10-1742905, is required to be coupled to the barrel, so the appearance of the syringe is changed considerably, and the manipulating method of the syringe for holding the position of the plunger is different from the method of using a normal syringe, thereby causing medical practitioners inconvenience when using the syringe.

In addition, there is proposed a syringe for collecting thyroid tissue cell in Korean Patent No. 10-1113752, wherein multiple stopper holding grooves are formed in a piston rod, and stopper members which can be held in such stopper holding grooves are coupled to the barrel so that the stopper members are held in the stopper holding grooves and hold the position of the piston rod. However, as for the syringe proposed in Korean Patent No. 10-1113752, an elastic piece is required to be used such that the stopper members are coupled to or removed from the stopper holding grooves at a desired position. Additionally, the syringe is difficult to be applied to an actual syringe due to the difficulty of injection design for the elaborate formation of the stopper holding grooves. Furthermore, the stopper members are coupled integrally to the piston rod to have the same directionality, so the vertical position manipulation of the piston rod is difficult.

Accordingly, it is necessary to have a new fat suction and graft syringe which has no big difference from a normal syringe in appearance and size, and minimizes the manipulation of a medical practitioner required to maintain negative pressure inside the barrel while the plunger is moved rearward and to push the plunger forward for the grafting of suctioned fat so that the usability of the syringe used by the medical practitioner is improved.

DISCLOSURE

Technical Problem

The present invention has been made keeping in mind the above problems occurring in the related art, and the present invention is intended to propose a fat suction and graft syringe having a negative pressure adjustment means, wherein the negative pressure adjustment means is provided with a multi-level holding plate composed of at least one plate vertically arranged in inner space between partition walls of a plunger and dividing the inner space between the partition walls into multi-level areas; a single-surface rotation clip configured to be coupled to a side of the entrance of a barrel and having a bent part which is rotated only upward and is not rotated downward; and a holding plate avoidance part supplying space allowing pressure applied to the single-surface rotation clip by the multi-level holding plate to be removed such that the single-surface rotation clip is moved to the space, whereby during fat suction and grafting procedures, the state of negative pressure inside the barrel is maintained only by pulling and releasing the plunger, and the multi-level holding plates do not interfere with the single-surface rotation clip only by slightly rotating the plunger such that the plunger is pushed inside, thereby improving usability such that many medical practitioners accustomed to the use of a normal syringe can easily use the syringe even without separately learning how to manipulate the syringe, and improving manufacturability.

Technical Solution

In order to achieve the above objectives, according to one aspect of the present invention, there is provided a fat suction and graft syringe having a negative pressure adjustment means, the syringe having a plunger moving forward and rearward by being inserted into a barrel which is empty and a needle coupled to an end of the barrel by a connector, the syringe including: the negative pressure adjustment means supplying pressure allowing fat to be suctioned into the barrel by maintaining an inner space between an end of the plunger and the end of the barrel at a state of negative pressure during the rearward movement of the plunger, wherein the negative pressure adjustment means includes:

a multi-level holding plate formed in an inner space between partition walls of the plunger having a cross-shaped structure formed by the partition walls, the multi-level holding plate composed of at least one plate being formed perpendicularly to the partition walls and dividing the inner space between the partition walls into multi-level areas; and a single-surface rotation clip coupled to a side of an entrance of the barrel and having a bent part configured to be rotated only upward and not to be rotated downward.

In this case, the multi-level holding plate may be installed at every position at which a size of the inner space of the barrel in which the state of negative pressure is generated is increased by 10 cc such that the multi-level holding plates are spaced apart from each other.

In addition, the single-surface rotation clip may include:

a rotation clip fixing part being open at a first side thereof and closed at a second side thereof, and configured to have a U shape such that the rotation clip fixing part is coupled to the barrel by fitting an inner space of the rotation clip fixing part over a finger support formed on an upper circumference of the barrel; a holding plate support part constituting a horizontal part of the bent part and coupled rotatably upward and downward to an end of the rotation clip fixing part, the holding plate support part supporting a lower surface of any one of the multi-level holding plates and having a plate shape; and an inner wall support part constituting a vertical part of the bent part and formed downward perpendicularly to an end of the holding plate support part, the inner wall support part supporting an inner wall of the barrel by having an L shape in cooperation with the holding plate support part and preventing the downward rotation of the holding plate support part.

Furthermore, the negative pressure adjustment means may further include a holding plate avoidance part supplying a space allowing pressure applied to the holding plate support part by the multi-level holding plate to be removed such that the plunger is moved forward without being restrained by the single-surface rotation clip.

In this case, the holding plate avoidance part may be configured as a vertical avoidance part formed by defining a vertical space in the inner space between the partition walls which has the multi-level holding plates by cutting a portion of each plate constituting the multi-level holding plates at a corresponding position to each other so that the plunger moves forward without being held by the holding plate support part.

Additionally, the holding plate avoidance part may be configured as a horizontal avoidance part comprising: a passing slot formed in a partition wall positioned at a side of the lower surface of each plate constituting the multi-level holding plates such that the holding plate support part passes through the partition wall of the plunger via the passing slot; and a vertical space defined in a space adjacent to the passing slot which does not have the multi-level holding plates such that the plunger moves forward without being held by the holding plate support part.

In addition, each of the multi-level holding plate and the holding plate avoidance part may be in each space between two partition walls facing each other of the space between the partition walls of the plunger.

Advantageous Effects

According to the syringe of the present invention, since the multi-level holding plate is held by the holding plate support part of the single-surface rotation clip only by pulling and releasing the plunger, the plunger is prevented from being moved forward, whereby a medical practitioner can maintain the inner space of the barrel at the state of negative pressure even without additional manipulation during a fat suction procedure.

In addition, according to the syringe of the present invention, the multi-level holding plate is formed at every position at which the size of the inner space in which the state of negative pressure is produced is increased by a predetermined degree, whereby the multi-level holding plate located at a position desired by a medical practitioner is held by the single-surface rotation clip and thus the amount of fat which the medical practitioner intends to suction can be easily determined.

Furthermore, according to the syringe of the present invention, the plunger can be pushed inside forward without the multi-level holding plate interfering with the single-surface rotation clip only by slightly rotating the plunger, whereby many medical practitioners accustomed to the use of a normal syringe can easily use the syringe having the negative pressure adjustment means even without separately learning how to manipulate the syringe.

Additionally, according to the syringe of the present invention, the configuration of the multi-level holding plates and the holding plate avoidance part formed between the partition walls of the plunger is simplified and the configuration of the single-surface rotation clip coupled to the barrel is also simplified, whereby the injection molding and manufacturability of the negative pressure adjustment means can be improved compared to prior negative pressure maintaining means in which a small holding plate or a coupling structure is required.

BEST MODE

Hereinafter, the exemplary embodiments of the present invention will be described in detail with reference to the accompanying drawings.

Figure 1:
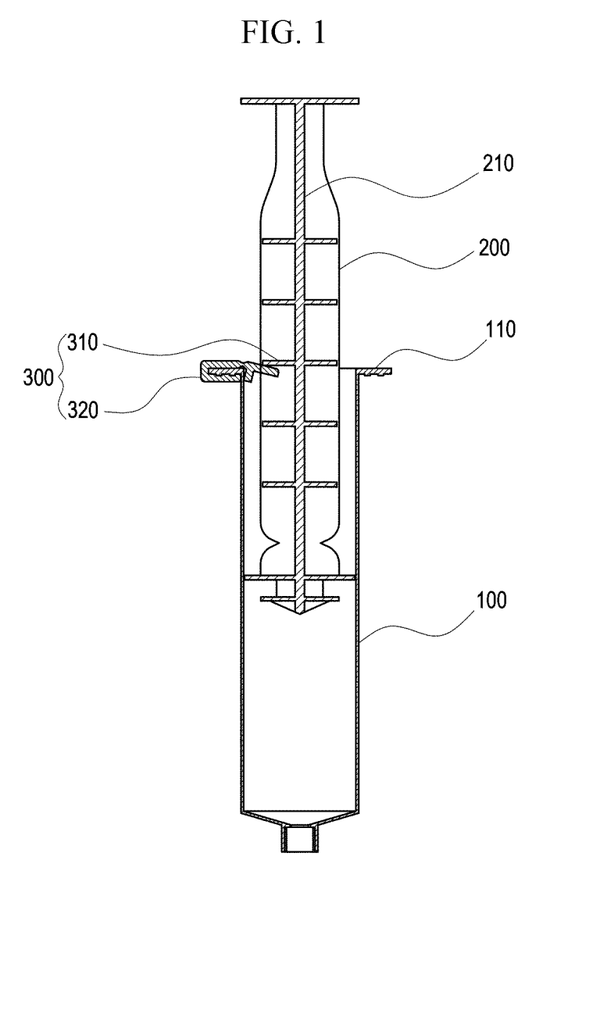
FIGS. 1 and 2 are front views of a fat suction and graft syringe having a negative pressure adjustment means according to the present invention.
Figure 2:
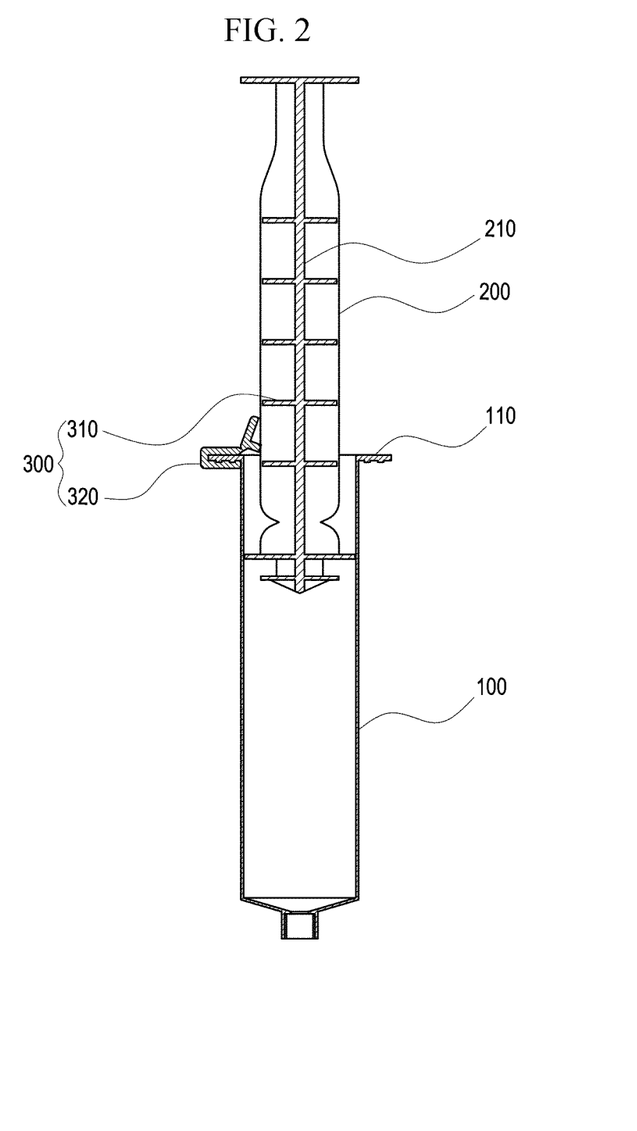

FIGS. 1 and 2 are front views of a fat suction and graft syringe having a negative pressure adjustment means according to the present invention. As illustrated in FIG. 1, when about half of a plunger is pulled out rearward, a multi-level holding plate is held by a single-surface rotation clip, and the plunger is prevented from being pulled inside forward to maintain the state of negative pressure. As illustrated in FIG. 2, while the plunger is being pulled rearward, the single-surface rotation clip is rotated upward, and the plunger is pulled outside without being restrained by the multi-level holding plate.

Referring to FIGS. 1 and 2, the fat suction and graft syringe having a negative pressure adjustment means according to the present invention, the syringe having a barrel 100 being empty therein, the plunger 200 moving forward and rearward by being inserted into the barrel 100, and a needle (not shown) coupled to an end of the barrel by a connector, includes the negative pressure adjustment means 300 supplying pressure allowing fat to be suctioned into the barrel by maintaining an inner space between an end of the plunger and the end of the barrel at the state of negative pressure during the rearward movement of the plunger.

In this case, the negative pressure adjustment means 300 is configured to include: the multi-level holding plate 310 provided in inner space between the partition walls of the plunger having a cross-shaped structure formed by the partition walls, the multi-level holding plate composed of at least one plate being formed perpendicularly to the partition walls and dividing the space between the partition walls into multi-level areas; and the single-surface rotation clip 320 coupled to a side of the entrance of the barrel and having a bent part configured to be rotated only upward and not to be rotated downward.

As illustrated in FIGS. 1 and 2, the multi-level holding plate 310 is formed in the space between partition walls 210 having the cross shape constituting the plunger 200 such that the multi-level holding plate is perpendicular to the partition walls, and is configured to have multiple multi-level holding plates such that any one of the multiple multi-level holding plates of the plunger pulled rearward can be held by the single-surface rotation clip 320.

Such multi-level holding plates 310 are formed perpendicularly to the partition walls by being spaced apart by a predetermined distance from each other, whereby an area allowing the single-surface rotation clip rotated upward during the rearward movement of the plunger to be restored to an initial state thereof is preferably provided in the space between the multi-level holding plates.

In addition, according to the degree of the rearward movement of the plunger, the size of an inner space defined between the end of the plunger and the end of the barrel is determined. Accordingly, the degree to which the multi-level holding plates 310 are spaced apart from each other is preferably configured to be constant so that the size of the inner space in which the state of negative pressure is produced is easily recognized. That is, the multi-level holding plate 310 is formed at every position at which the size of the inner space in which the state of negative pressure is produced increases by 10 cc, and the multi-level holding plate located at a position desired by a medical practitioner is held by the single-surface rotation clip, so the amount of fat which the practitioner intends to suction can be easily determined.

For example, in the case of a 50 cc syringe, the multi-level holding plate is formed at every position at which inner space in which fat of 10 cc can be suctioned is defined, and a total of five multi-level holding plates are installed to be spaced apart from each other. Accordingly, a medical practitioner can hold a third, a fourth, or a fifth multi-level holding plate in the single-surface rotation clip according to the amount of fat which he or she intends to suction such that the amount of fat he or she intends to suction can be easily controlled.

Furthermore, the multi-level holding plate 310 is preferably configured to have height larger than a half of the height of each of the partition walls and to have height smaller than two thirds thereof such that the forward and rearward movements of the plunger inserted into the barrel are not prevented and the contacting area of each of the multi-level holding plates 310 with the holding plate support part constituting the single-surface rotation clip is sufficiently secured.

In addition, the multi-level holding plates 310 are vertically arranged in the space between the partition walls 210 of the plunger having the cross-shaped structure, each of the multi-level holding plates being preferably configured to have a fan shape having approximately one fourth of a circular shape according to the shape of the space between such partition walls.

The single-surface rotation clip 320 includes: the bent part 322 and 324 rotated upward by being held by each of the multi-level holding plates when the plunger is pulled rearward, but supporting the lower surface of the multi-level holding plate without being rotated when the plunger is pulled inside forward; and a rotation clip fixing part 326 coupled to a finger support provided on the barrel and supporting the pressure of the multi-level holding plate pressing the bent part.

Figure 4:
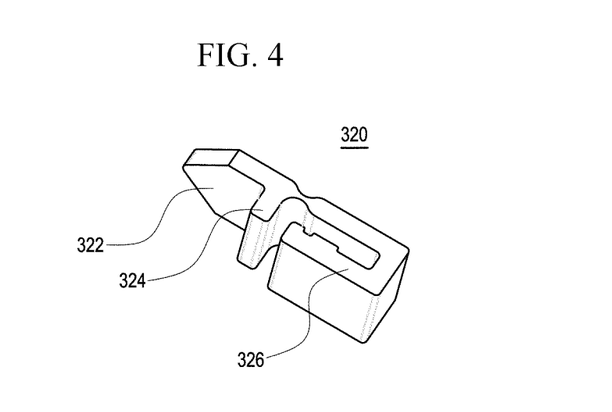
FIG. 4 is a bottom perspective view of a single-surface rotation clip according to the present invention.

In this case, as illustrated in FIG. 4, the bent part and the rotation clip fixing part constituting the single-surface rotation clip may be configured to have an integral shape connected to each other. However, in this case, stress is focused on a portion at which the rotation of the bent part is performed, and the portion may be broken. Accordingly, the bent part is preferably configured to be hinged rotatably to the rotation clip fixing part.

As illustrated in FIG. 4, the rotation clip fixing part 326 of such a single-surface rotation clip is open at a first side thereof and closed at a second side thereof, and is configured to have an approximate U shape such that the rotation clip fixing part 326 is coupled to the barrel 100 by fitting the inner space of the rotation clip fixing part 326 over the finger support 110 formed on the upper circumference of the barrel. Furthermore, a predetermined groove is preferably formed in the inner lower surface of the rotation clip fixing part 326 such that the rotation clip fixing part 326 can be stably coupled to the finger support of the barrel.

In addition, as illustrated in FIG. 4, the bent part of the single-surface rotation clip is coupled to the front surface of the open portion of the rotation clip fixing part 326 to be rotatable upward and downward, and includes: the holding plate support part 322 having a plate shape rotated upward by being held by the upper surface of the multi-level holding plate or pressed downward by being held by the lower surface of the multi-level holding plate; and an inner wall support part 324 formed downward perpendicularly to an end of the holding plate support part and supporting the inner wall of the barrel by having an L shape in cooperation with the holding plate support part, the inner wall support part 324 preventing the downward rotation of the holding plate support part.

Accordingly, in the bent part, the holding plate support part 322 which supports the lower surface of the multi-level holding plate, and the inner wall support part 324 which supports the inner wall of the barrel to prevent the downward rotation of the holding plate support part are connected to each other to have an L shape. Accordingly, even without a separate holding means such as a separate elastic means or small stopper, the bent part can be embodied to support the inner wall of the barrel by resisting a force of pulling the plunger inside due to negative pressure produced inside the barrel, and can embody a strong support resisting a larger force of pulling the plunger inside that may occur during the use of a large syringe.

That is, the holding plate support part 322 is allowed to be in contact with a large area of the multi-level holding plate 310, and can resist the pulling force generated due to the negative pressure of the inside of the barrel in the large area thereof. Accordingly, although the pulling force generated due to the negative pressure is increased, the holding plate support part 322 can stably support the multi-level holding plate since the holding plate support part 322 is in contact with the multi-level holding plate in the large area.

In addition, the pulling force generated due to the negative pressure causes the inner wall support part 324 to press only the inner wall of the barrel 100, so although the pulling force generated due to the negative pressure is increased, the inner wall support part 324 resists the increased pulling force without difficulty and prevents the plunger from being pulled inside.

Accordingly, the bent part composed of the holding plate support part 322 and the inner wall support part 324 is mounted to the rotation clip fixing part 326 to be rotated in opposite directions, and the downward rotation of the bent part caused by the state of negative pressure produced inside the barrel is prevented by the inner wall support part 324 supporting the inner wall of the barrel. Accordingly, the single-surface rotation clip which is high in durability and is easily injection molded can be embodied.

In addition, in the syringe having a fat suction and graft syringe having a negative pressure adjustment means according to the present invention, the suction of fat is required to be performed with the state of negative pressure maintained, and the plunger is required to be moved forward to graft the fat to another area of the body after the fat suction is completed.

Accordingly, to move the plunger forward without having the plunger restrained by the single-surface rotation clip, the negative pressure adjustment means 300 is preferably configured to further include a holding plate avoidance part supplying space in which pressure applied to the holding plate support part by the multi-level holding plate is removed.

Figure 3:
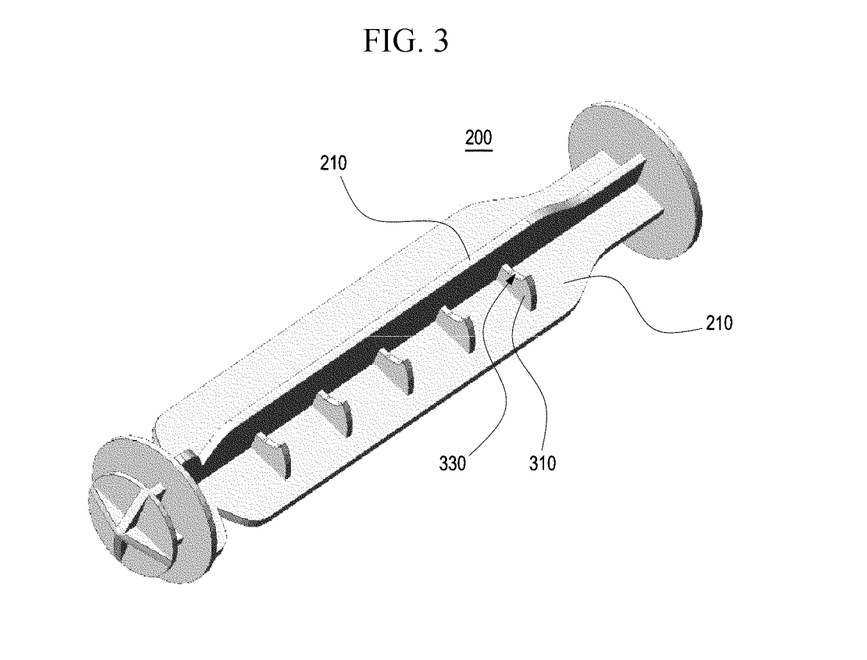
FIG. 3 is a perspective view of a plunger according to a first embodiment of the present invention.

As illustrated in FIG. 3 according to the first embodiment, such a holding plate avoidance part may be configured as a vertical avoidance part 330 having a vertical space defined in the inner space between the partition walls which has the multi-level holding plates such that the plunger moves forward without being held by the holding plate support part. Alternatively, as illustrated in FIG. 8 according to a second embodiment, the holding plate avoidance part may be configured as a horizontal avoidance part 340 having a vertical space defined in an adjacent space without having the multi-level holding plates which is adjacent to the space having the multi-level holding plates such that the plunger moves forward without being held by the holding plate support part.

In this case, as illustrated in FIG. 3, the vertical avoidance part 330 is formed by defining a vertical space in the inner space between the partition walls which has the multi-level holding plates by cutting a portion of each plate constituting the multi-level holding plates 310 such that the plunger 200 is moved forward and rearward without being held by the holding plate support part 322, the vertical space allowing the holding plate support part 322 to move therein. Accordingly, as illustrated in FIG. 3, the multi-level holding plate 310 is formed by cutting a portion of a fan shape having the shape of a fourth of a circular shape.

As illustrated in FIG. 3, an area of each of the multi-level holding plates partially cut to form such a vertical avoidance part is formed at the corresponding position of each of the multi-level holding plates. Accordingly, after the holding plate support part 322 reaches the cut area constituting the vertical avoidance part 330 by rotating the plunger 200, the forward movement of the plunger can preferably be performed without additional manipulation.

Figure 8:
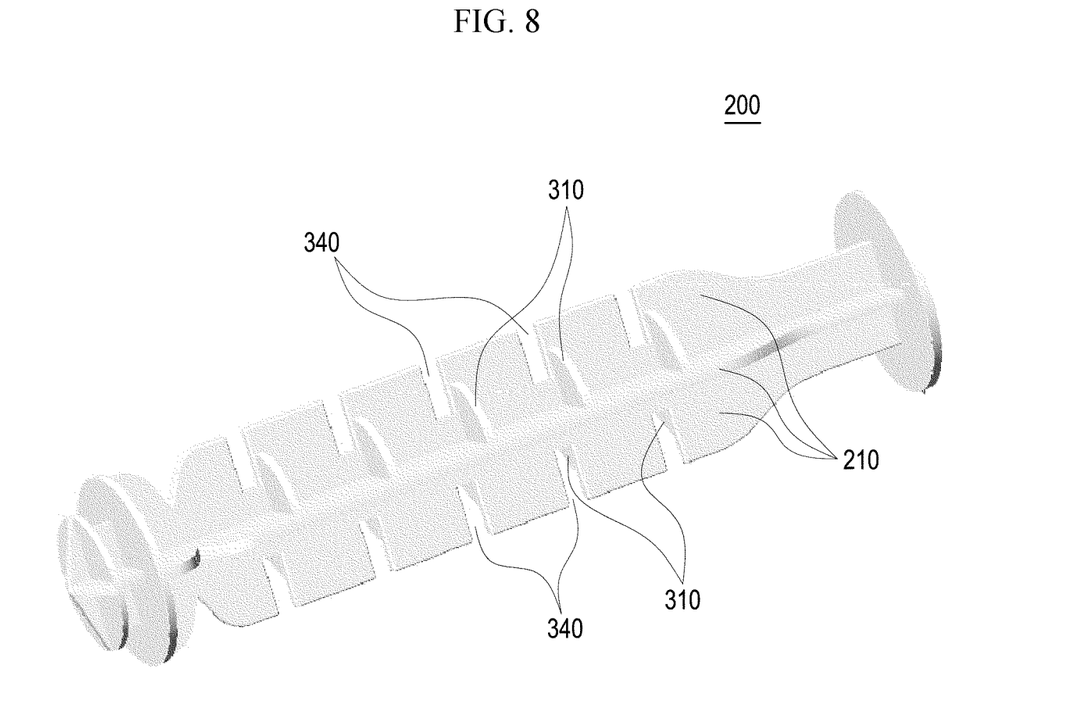
FIG. 8 is a perspective view of a plunger according to a second embodiment of the present invention.

In addition, as illustrated in FIG. 8, to move the plunger 200 forward and rearward without the plunger being held by the holding plate support part, the horizontal avoidance part 340 includes the passing slot formed in the partition wall positioned at the side of the lower surface of each plate constituting the multi-level holding plates such that the holding plate support part 322 passes through the partition wall 210 of the plunger via the passing slot, and a vertical space defined in space adjacent to the passing slot which does not have the multi-level holding plates such that the holding plate support part moves in the vertical space.

To form such a horizontal avoidance part 340, the passing slot through which the holding plate support part 322 can pass is formed in the partition wall 210 positioned at the side of the lower surface of each of the multi-level holding plates 310 as illustrated in FIG. 8. Accordingly, at any position at which the holding plate support part is held by the multi-level holding plate, like a plunger of a normal syringe, the plunger can be moved forward only by being rotated.

Accordingly, like the multi-level holding plates, the vertical avoidance part 330 illustrated in FIG. 3 and the horizontal avoidance part 340 illustrated in FIG. 8 may be formed in each of spaces opposite to each other of the spaces between the partition walls of the plunger having a cross-shaped structure. In FIG. 3, the vertical avoidance part at a side opposite to the shown vertical avoidance part is not shown due to the partition walls, but in FIG. 8, the passing slot is illustrated to be formed in each of two partition walls.

Figure 5:
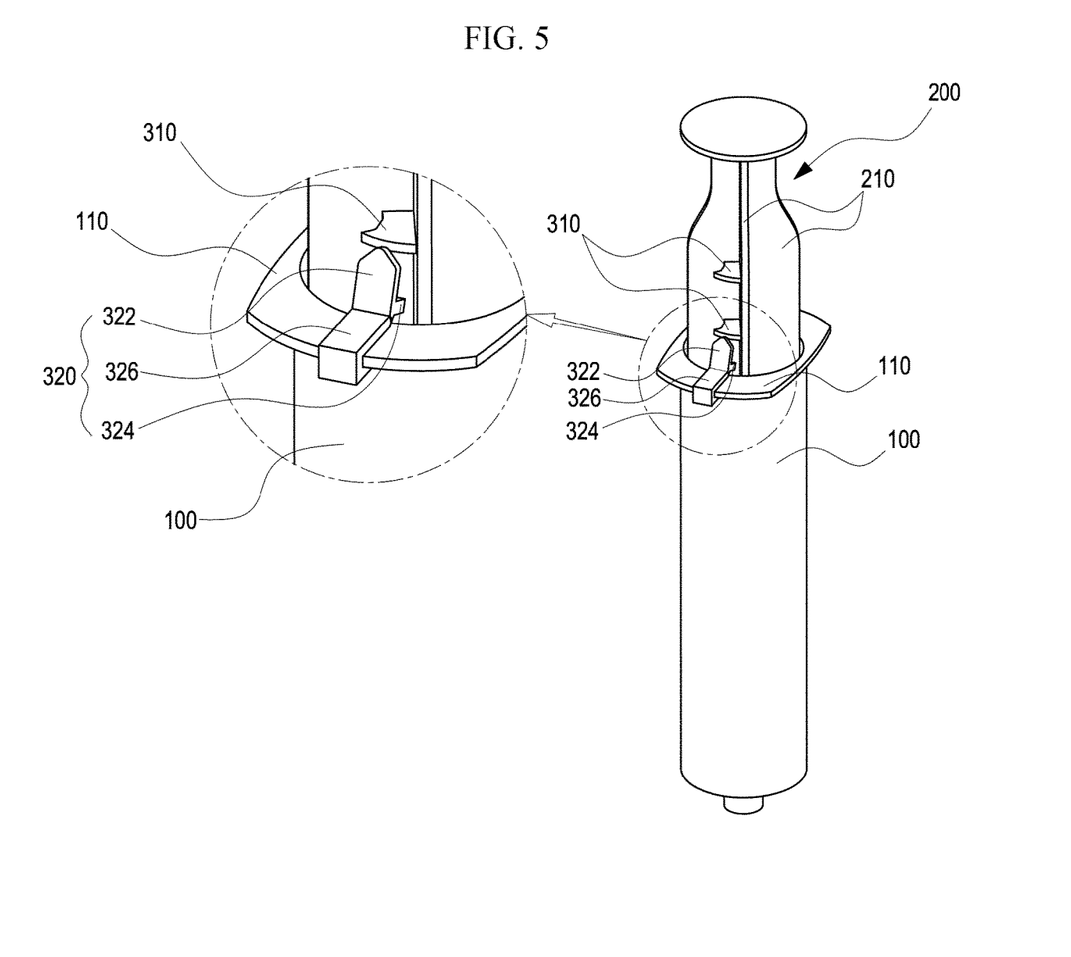
FIG. 5 is a view illustrating the plunger which is being removed from a barrel according to the present invention.
Figure 6:
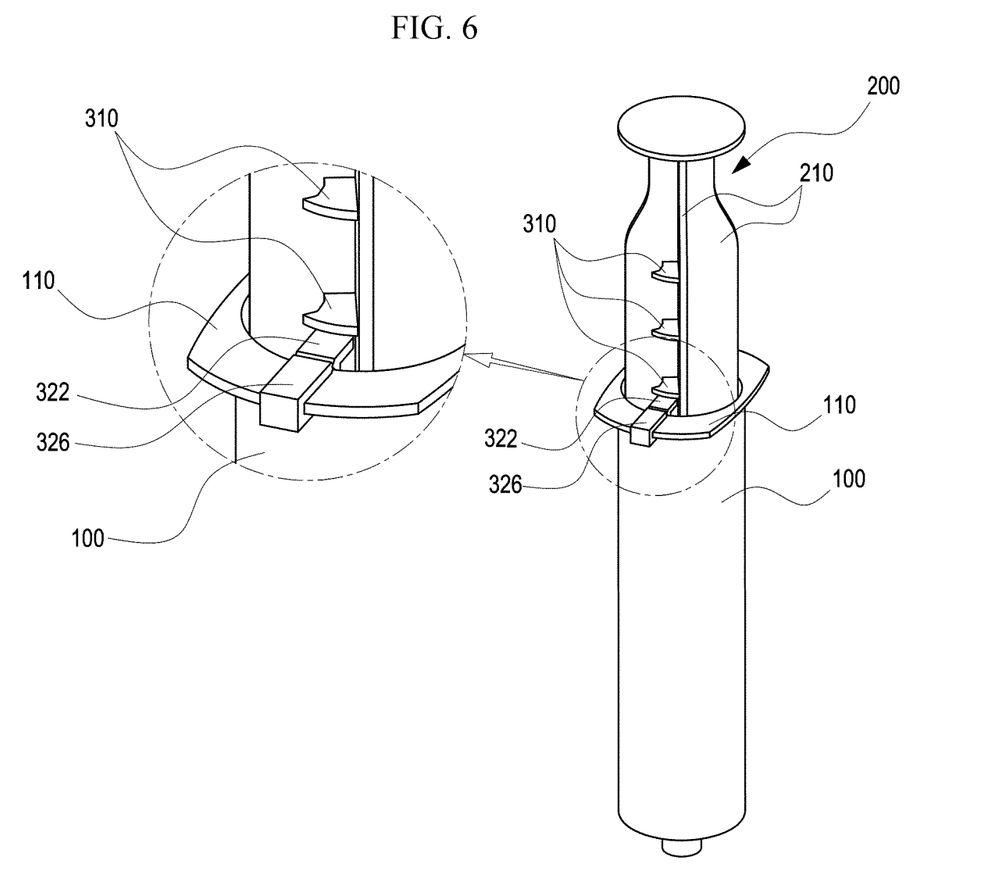
FIG. 6 is a view illustrating the inside of the barrel maintained at the state of negative pressure due to the plunger held by a multi-level holding plate according to the present invention.
Figure 7:
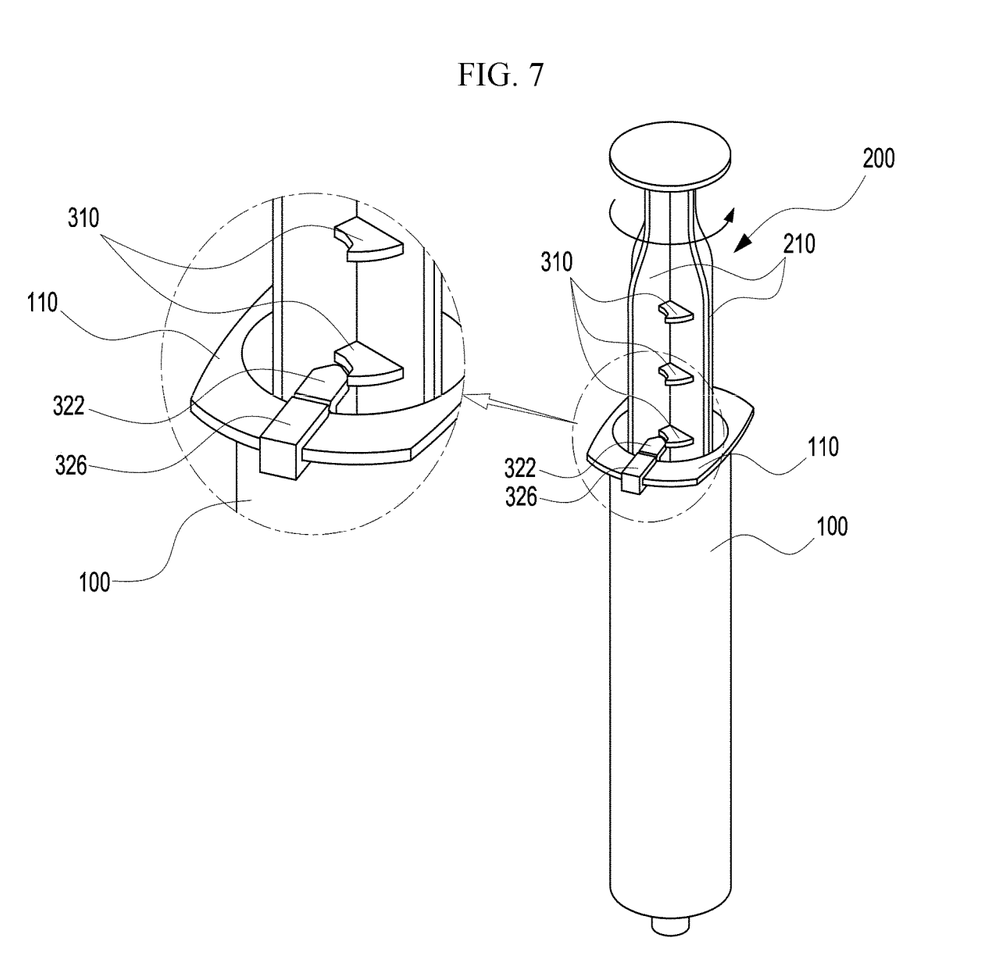
FIG. 7 is a view illustrating the releasing of the state of negative pressure of the inside of the barrel by rotating the plunger according to the present invention.
Figure 9:
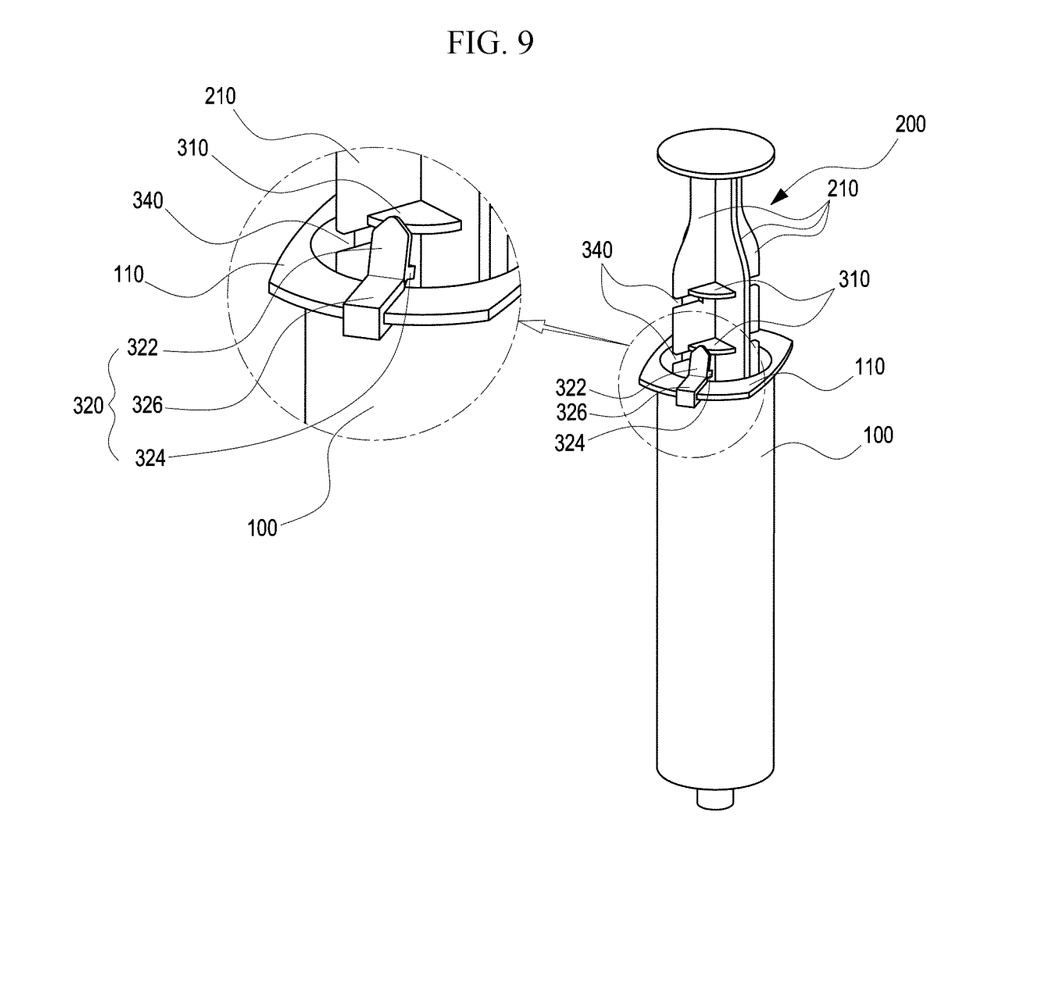
FIGS. 9 to 11 are views sequentially illustrating the maintaining and releasing of the state of negative pressure of the inside of the barrel according to the second embodiment of the present invention.
Figure 10:
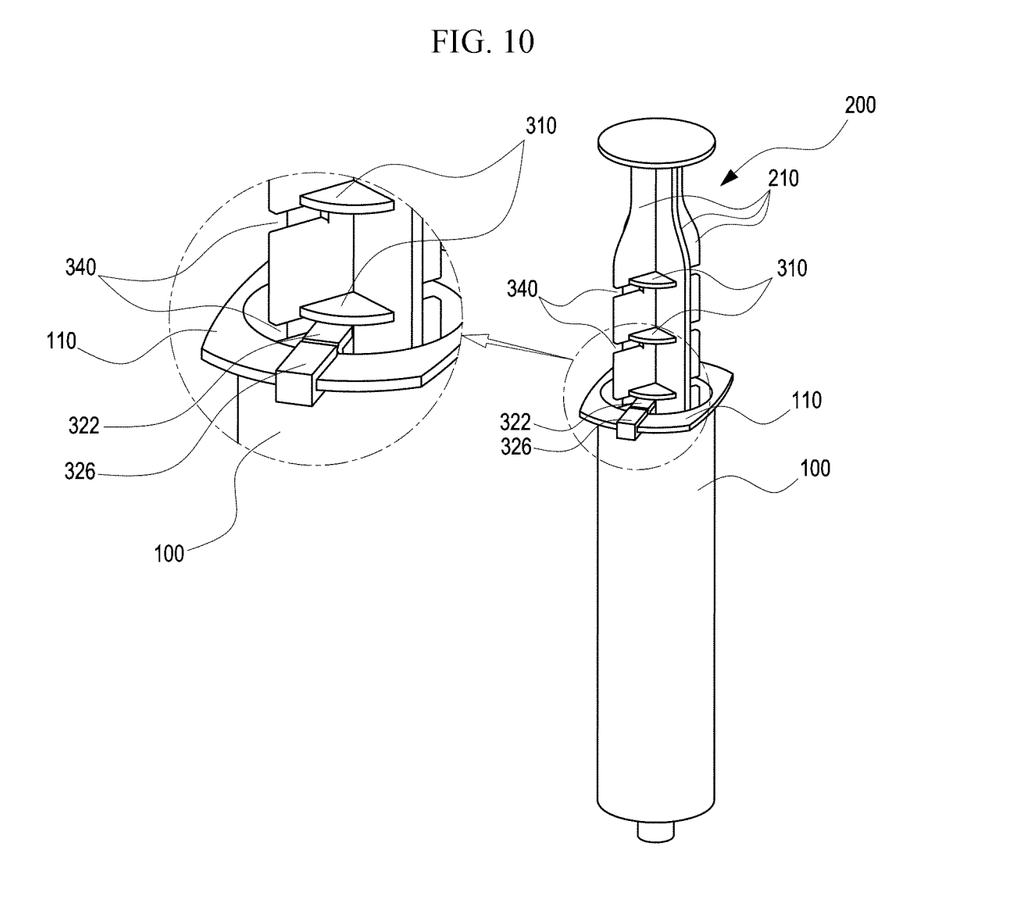
Figure 11:
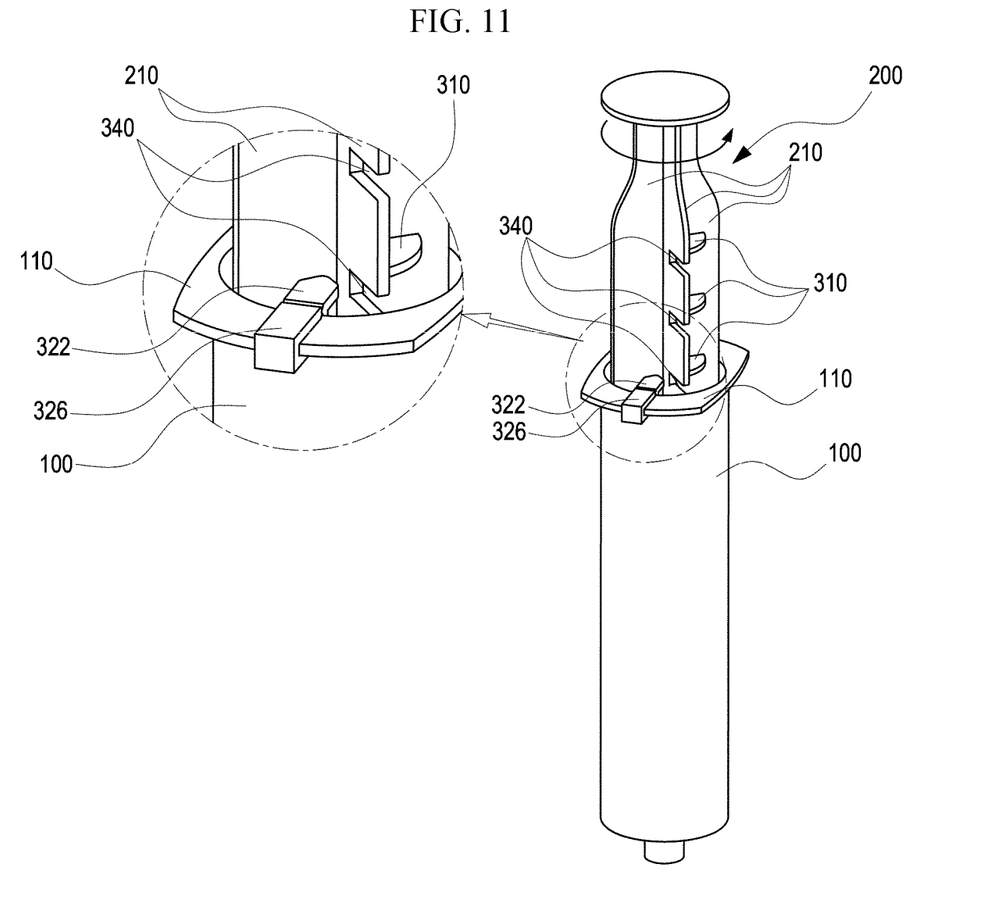

Next, in the fat suction and graft syringe having a negative pressure adjustment means which has the above-described configuration according to the present invention, the processes in which the rearward movement of the plunger for the suction of fat, the maintenance of the state of negative pressure, and the forward movement of the plunger for fat grafting are performed will be described with reference to FIGS. 5 to 7 illustrating the holding plate avoidance part according to the first embodiment, and with reference to FIGS. 9 to 11 illustrating the holding plate avoidance part according to the second embodiment.

First, referring to FIGS. 5 to 7, due to the holding plate avoidance part according to the first embodiment, the forward movement of the plunger is performed by a medical practitioner's manipulation after the state of negative pressure of the plunger is maintained.

For the suction of fat, when the plunger 200 inserted into the barrel 100 is pulled rearward, negative pressure is produced in the inner space between the end of the plunger and the end of the barrel, and such negative pressure generates a suction power to suction broken-down fat into the inner space through the needle which is the only passage.

In this case, as illustrated in FIG. 5, while the plunger is pulled rearward, the multi-level holding plates 310 installed between the partition walls of the plunger contact with the holding plate support part 322 of the single-surface rotation clip 320 coupled to the barrel. The holding plate support part 322 is rotated upward without resistance by the force of each of the multi-level holding plates applied upward to the holding plate support part 322 relative to the combining portion of the rotation clip fixing part 326 with the bent part. Accordingly, a medical practitioner can produce the state of negative pressure inside the barrel by moving the plunger rearward like the use of a normal syringe.

Next, when the plunger 200 is released at a position at which a medical practitioner intends the plunger to stop, the plunger is pulled inside forward due to the negative pressure produced in the inner space between the end of the plunger and the end of the barrel. In this case, as illustrated in FIG. 6, the lower surface of the multi-level holding plate 310 is in contact with and presses down the upper surface of the holding plate support part 322 of the single-surface rotation clip.

Accordingly, the holding plate support part 322 is pressed by the pressure of the lower surface of the multi-level holding plate pressing the holding plate support part, and the inner wall support part 324 formed by being bent perpendicularly to the end of the holding plate support part presses the inner wall of the barrel, whereby the holding plate support part is not rotated in a downward direction and in this state, supports the multi-level holding plate 310. Accordingly, while the holding plate support part supports the multi-level holding plate, the inner space of the barrel maintains the state of negative pressure. Accordingly, a medical practitioner can maintain the state of negative pressure even without making any other efforts during the fat suction.

That is, to maintain the state of negative pressure by using a prior normal a fat suction and graft syringe, a barrel is required to be held by one hand, and a plunger is required to be pulled by the other hand. To hold the plunger at a position to which the plunger is pulled, another assistant's help is required or a separate holding means is required to be coupled thereto except for the hand holding the barrel or the hand holding the plunger. However, in the case of the use of the fat suction and graft syringe having a negative pressure adjustment means according to the present invention, when the plunger is pulled and released at a desired position in the same way as the case of the use of a normal syringe, the plunger which is being pulled inside stops automatically at a specific position and the state of negative pressure can be maintained. Accordingly, even in the case of the use of a large syringe of 50 cc or 100 cc, a medical practitioner alone can easily maintain the state of negative pressure during a fat suction procedure.

Next, when the plunger is required to be pushed toward the inside of the barrel for fat grafting after the fat suction and an intended procedure are completed, as illustrated in FIG. 7, the plunger 200 is rotated counterclockwise, and the vertical avoidance part 330 which does not have the multi-level holding plate is located at the upper side of the holding plate support part 322. In this case, the plunger is rotated while being slightly pulled rearward, so the rotation of the plunger is performed while the lower surface of the multi-level holding plate is spaced apart from the holding plate support part, thereby improving manipulability.

Accordingly, after the holding plate support part 322 is located in the vertical avoidance part 330 which does not have the multi-level holding plate by rotating the plunger 200, the plunger can be pushed inside forward without being restrained by the single-surface rotation clip.

Next, referring to FIGS. 9 to 11, due to the holding plate avoidance part according to the second embodiment, the forward movement of the plunger is performed by a medical practitioner's manipulation after the state of negative pressure of the plunger is maintained.

As illustrated in FIGS. 9 and 10, when the plunger is pulled rearward, the plunger is moved rearward while the holding plate support part 322 of the single-surface rotation clip is rotated upward by the multi-level holding plates 310, and the state of negative pressure is produced in the inner space between the end of the plunger and the end of the barrel. When the plunger 200 is released at a desired position, the lower surface of the multi-level holding plate 310 provided in the plunger which is being pulled inside forward is in contact with the upper surface of the holding plate support part 322 of the single-surface rotation clip, and the plunger stops. Accordingly, it is the same as the above-described first embodiment that the inner space of the barrel can be maintained at the state of negative pressure without a medical practitioner's any other efforts or manipulation.

In this case, in the second embodiment, the multi-level holding plates arranged vertically in the inner space between the partition walls of the plunger block the entirety of the inner space. Accordingly, although the plunger is slightly rotated due to the slight movement or shaking of the syringe which may occur during a fat suction procedure, the holding plate support part may still support the lower surface of the multi-level holding plate as long as the holding plate support part is located in the inner space between the partition walls.

Next, as illustrated in FIG. 11, when the plunger 200 is rotated counterclockwise to push the plunger toward the inside of the barrel, the holding plate support part 322 passes through the passing slot, which constitutes the horizontal avoidance part 340, formed in the partition wall and moves to the space between the partition walls 210 adjacent to the passing slot in which the multi-level holding plates are not formed. Accordingly, due to the rotation of the plunger 200, the single-surface rotation clip 320 passes through the partition wall 210 and is located in the space between the partition walls in which the multi-level holding plates are not formed, whereby like a normal syringe, the plunger can be pushed inside without the multi-level holding plates restrained by the single-surface rotation clip.

Accordingly, according to the present invention, like a normal syringe, during fat suction and grafting procedures, the state of negative pressure inside the barrel is maintained only by pulling and releasing the plunger, and the multi-level holding plates do not interfere with the single-surface rotation clip only by rotating the plunger, so like the normal syringe, the plunger can be pushed in. Accordingly, many medical practitioners accustomed to the use of the normal syringe can easily use the syringe without separately learning how to manipulate the syringe.

In the above, the technical idea for the present invention has been described with reference to the accompanying drawings, but the drawings are intended to describe the exemplary embodiments of the present invention, but do not limit the present invention. In addition, it is obvious that anyone with ordinary knowledge in the technical field to which the present invention belongs can make various modifications and imitations within the scope of the technical idea of the present invention.

DESCRIPTION OF THE REFERENCE NUMERALS IN THE DRAWINGS

100: Barrel 110: Finger support
200: Plunger 210: Partition wall
300: Negative pressure adjustment means 310: Multi-level holding plate
320: Single-surface rotation clip 322: Holding plate support part
324: Inner wall support part 326: Rotation clip fixing part
330: Vertical avoidance part 340: Horizontal avoidance part

INDUSTRIAL APPLICABILITY

The syringe of the present invention has high industrial applicability in that since the multi-level holding plate is held by the holding plate support part of the single-surface rotation clip only by pulling and releasing the plunger, the plunger is prevented from being moved forward, whereby a medical practitioner can maintain the inner space of the barrel at the state of negative pressure even without additional manipulation during a fat suction procedure.

In addition, the syringe of the present invention has high industrial applicability in that the multi-level holding plate is formed at every position at which the size of the inner space in which the state of negative pressure is produced is increased by a predetermined degree, whereby the multi-level holding plate located at a position desired by a medical practitioner is held by the single-surface rotation clip and thus the amount of fat which the medical practitioner intends to suction can be easily determined.

Furthermore, the syringe of the present invention has high industrial applicability in that the plunger can be pushed inside forward without the multi-level holding plate interfering with the single-surface rotation clip only by slightly rotating the plunger, whereby many medical practitioners accustomed to the use of a normal syringe can easily use the syringe having the negative pressure adjustment means even without separately learning how to manipulate the syringe.

Additionally, the syringe of the present invention has high industrial applicability in that the configuration of the multi-level holding plates and the holding plate avoidance part formed between the partition walls of the plunger is simplified and the configuration of the single-surface rotation clip coupled to the barrel is also simplified, whereby the injection molding and manufacturability of the negative pressure adjustment means can be improved compared to prior negative pressure maintaining means in which a small holding plate or a coupling structure is required.

The invention claimed is:

1. A fat suction and graft syringe comprising:
   a plunger movable forward and rearward by being inserted into a barrel which is empty;
   a needle coupled to an end of the barrel by a connector; and
   a negative pressure adjustment means supplying pressure allowing fat to be suctioned into the barrel by maintaining an inner space between an end of the plunger and the end of the barrel at a state of negative pressure during the rearward movement of the plunger,
   wherein the negative pressure adjustment means comprises:
   a multi-level holding plate formed in an inner space between partition walls of the plunger having a cross-shaped structure formed by the partition walls, the multi-level holding plate composed of at least one plate being formed perpendicularly to the partition walls and dividing the inner space between the partition walls into multi-level areas;
   and a single-surface rotation clip coupled to a side of an entrance of the barrel and having a bent part configured to be rotated only upward and not to be rotated downward by interacting with the multi-level holding plate during movement of the plunger;
   wherein the single-surface rotation clip comprises:
   a rotation clip fixing part being open at a first side thereof and closed at a second side thereof, and configured to have a U shape such that the rotation clip fixing part is coupled to the barrel by fitting an inner space of the rotation clip fixing part over a finger support formed on an upper circumference of the barrel;
   a holding plate support part constituting a horizontal part of the bent part and coupled rotatably upward and downward to an end of the rotation clip fixing part, the holding plate support part supporting a lower surface of any one of the multi-level holding plates and having a plate shape;
   and an inner wall support part constituting a vertical part of the bent part and formed downward perpendicularly to an end of the holding plate support part, the inner wall support part supporting an inner wall of the barrel by having an L shape in cooperation with the holding plate support part and preventing the downward rotation of the holding plate support part.

2. The syringe of claim 1, wherein the multi-level holding plate is installed at every position at which a size of the inner space of the barrel in which the state of negative pressure is generated is increased by 10 cc such that the multi-level holding plates are spaced apart from each other.

3. The syringe of claim 1, wherein the negative pressure adjustment means further comprises a holding plate avoidance part supplying a space allowing pressure applied to the holding plate support part by the multi-level holding plate to be removed such that the plunger is moved forward without being restrained by the single-surface rotation clip.

4. The syringe of claim 3, wherein the holding plate avoidance part is configured as a vertical avoidance part formed by defining a vertical space in the inner space between the partition walls which has the multi-level holding plates by cutting a portion of each plate constituting the multi-level holding plates at a corresponding position to each other so that the plunger moves forward without being held by the holding plate support part.

5. The syringe of claim 4, wherein each of the multi-level holding plate and the holding plate avoidance part is formed in each space between two partition walls facing each other of the space between the partition walls of the plunger.

6. The syringe of claim 3, wherein the holding plate avoidance part is configured as a horizontal avoidance part comprising: a passing slot formed in a partition wall positioned at a side of the lower surface of each plate constituting the multi-level holding plates such that the holding plate support part passes through the partition wall of the plunger via the passing slot; and a vertical space defined in a space adjacent to the passing slot which does not have the multi-level holding plates such that the plunger moves forward without being held by the holding plate support part.

7. The syringe of claim 6, wherein each of the multi-level holding plate and the holding plate avoidance part is formed in each space between two partition walls facing each other of the space between the partition walls of the plunger.

* * * * *